US007918862B2

(12) United States Patent
Hull, Jr. et al.

(10) Patent No.: US 7,918,862 B2
(45) Date of Patent: Apr. 5, 2011

(54) WATER-RESISTANT DEVICES INCORPORATING A SWITCH ASSEMBLY

(75) Inventors: Raymond J. Hull, Jr., Hampton, NJ (US); Shu Wong Lau, New Territories (HK)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 1513 days.

(21) Appl. No.: 11/287,560

(22) Filed: Nov. 23, 2005

(65) Prior Publication Data

US 2007/0114117 A1 May 24, 2007

(51) Int. Cl.
*A61B 17/50* (2006.01)

(52) U.S. Cl. ........................................ 606/131; 604/290

(58) Field of Classification Search .......... 606/132–134, 606/131; 601/53, 72, 73, 89; 335/114, 115, 335/120, 122, 126, 127, 190; 604/290
See application file for complete search history.

(56) References Cited

U.S. PATENT DOCUMENTS

| | | | | |
|---|---|---|---|---|
| 4,709,310 | A | 11/1987 | Ohashi | |
| 4,799,280 | A * | 1/1989 | Lee | 15/29 |
| 4,964,398 | A | 10/1990 | Jones | |
| 7,306,569 | B2 * | 12/2007 | LaJoie et al. | 601/70 |
| 2003/0229300 | A1 | 12/2003 | Winkley | |

FOREIGN PATENT DOCUMENTS

| | | | |
|---|---|---|---|
| CN | 2357728 | Y | 1/2000 |
| DE | 198 18 745 | A | 10/1999 |
| EP | 0 311 178 | A | 4/1989 |
| EP | 1 666 016 | A | 6/2006 |
| GB | 2 178 153 | A | 2/1987 |
| GB | 2 253 512 | A | 9/1992 |
| WO | WO 2005/025478 | A | 3/2005 |

* cited by examiner

*Primary Examiner* — Todd E Manahan
*Assistant Examiner* — Michael G Mendoza

(57) ABSTRACT

An electric-powered device includes (1) a skin-contactable surface and (2) a body having a water-resistant switch assembly. Preferably, the electric-powered device is useful in skin treatment and delivers mechanical forces on the skin. The switch assembly preferably includes, a substantially planar mount having an aperture, a rotatable shaft extending through the aperture, and a seal lining the aperture to restrict water movement along the shaft. In another aspect a water-resistant switch assembly includes first translatable element adapted for substantially planar motion in a first plane; a rotatable shaft, engageable with said first translatable element; a second translatable element adapted for substantially planar motion in a second plane, wherein said second translatable element is engageable with said rotatable shaft; a substantially planar mount having a through-hole and defining a third plane, wherein said rotatable shaft pierces said through hole and said third plane, wherein said third plane is substantially between said second plane and said third plane; and a seal surrounding said through-hole for rendering said through hole water-resistant.

4 Claims, 5 Drawing Sheets

WATER-RESISTANT DEVICES INCORPORATING A SWITCH ASSEMBLY

BACKGROUND OF THE INVENTION

The skin is the largest organ of the body and requires frequent care to remove dirt and debris. In addition, it is desirable for many individuals to provide other benefits to their skin, to prevent and/or treat various skin conditions. Examples of such skin conditions include signs of aging such as wrinkles, fine lines, age spots; acne; among other skin conditions.

Numerous techniques have been proposed to provide cleansing, cosmetic and/or therapeutic benefits to the skin. One technique is to employ a device, such as a portable device that can be used "at home" to effect changes in skin health and appearance. Accordingly, devices such as cleansing and microdermabrasion systems that combine a motorized apparatus and a skin-contacting surface are available. Users of such devices may apply water to the skin-contacting surface of the device to enhance overall performance.

Devices such as at home skin treatment devices, while safe and efficacious, are however susceptible to the infiltration of water into the device, e.g., particularly when water is applied to the skin-contacting surface. Applicants have recognized that water may inadvertently penetrate the device through the switch assembly, resulting in premature failure of the device. One solution for waterproofing the switch assembly is to overwrap the switch assembly in a rubber housing. Unfortunately, this approach is costly and adds manufacturing challenges. Accordingly, a need exists for a water-resistant switch assembly that is simple, easy to manufacture, and effective.

SUMMARY OF THE INVENTION

In one aspect of the invention, embodiments of the invention relate to an electric-powered device that includes (1) a skin-contactable surface and (2) a body having a water-resistant switch assembly. Preferably, the electric-powered device is useful in skin treatment and delivers mechanical forces on the skin. The switch assembly preferably includes, a substantially planar mount having an aperture, a rotatable shaft extending through the aperture, and a seal lining the aperture to restrict water movement along the shaft.

In another aspect, embodiments of the invention relates to a switch assembly. The switch assembly includes first translatable element adapted for substantially planar motion in a first plane; a rotatable shaft, engageable with said first translatable element; a second translatable element adapted for substantially planar motion in a second plane, wherein said second translatable element is engageable with said rotatable shaft; a substantially planar mount having a through-hole and defining a third plane, wherein said rotatable shaft pierces said through hole and said third plane, wherein said third plane is substantially between said second plane and said third plane; and a seal surrounding said through-hole for rendering said through hole water-resistant.

BRIEF DESCRIPTION OF THE DRAWINGS

A more particular description of the invention, briefly summarized above may be had by reference to the embodiments thereof that are illustrated in the appended drawings. It is to be so noted, however, that the appended drawings illustrate only typical embodiments of the invention and, therefore, are not to be considered limiting of its scope, for the invention may admit to other equally effective embodiments.

To facilitate understanding identical reference elements have been used, wherever possible, to designate identical elements that are common to the figures.

DETAILED DESCRIPTION OF THE INVENTION

It is believed that one skilled in the art can, based upon the description herein, utilize the present invention to its fullest extent. The following specific embodiments are to be construed as merely illustrative, and not limitative of the remainder of the disclosure in any way whatsoever.

The present invention is directed to a switch that is useful for reducing infiltration of water into a device. In various embodiments of the invention, such switches and devices provide waterproofing, ease of manufacture, relatively low production costs, and reduced space requirements.

Figure 1:
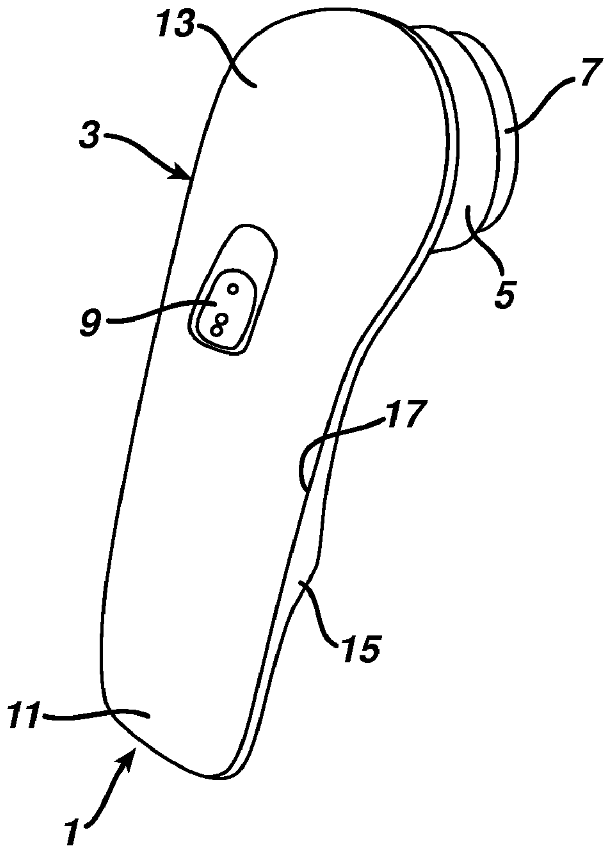
FIG. 1 is a perspective view of a device consistent with embodiments of the present invention.

FIG. 1 depicts one non-limiting example of a device 1 consistent with embodiments of invention described herein. The device 1 may be of varying shapes and dimensions, and one notable shape includes an elongated body 3 and a head region 5. The device 1 also generally includes one or more surfaces 7 for contacting or placing proximate the skin. A switch assembly 9 is provided for providing one or more levels of power to the device 1 to power a motor capable of delivering motion, such as vibration, to the surface 7.

In operation, an operator grasps the body 3 and empowers a battery-powered motor (not shown in FIG. 1) within the device 1, by actuating switch assembly 9. The motor, thereby empowered, provides energy that is transmitted to the attached surface 7 and to an expanse of skin placed in contact therewith. The energy may be of various forms (e.g., mechanical vibration, rotation, reciprocation, or optical, thermal, magnetic, among others) that is transmitted via various means, e.g., an eccentric weight, a reciprocating shaft or transfer member, a rotating disc, laser diode, magnet, and the like. The body 3 is generally shaped to facilitate easy grasping by the user so that the device 1 is oriented such that the attached skin-contactable surface 7 can contact or be placed proximate the user's skin.

In one notable embodiment, the device 1 is a microdermabrasion device, useful for abrading the skin and providing rejuvenation benefits thereto. In this embodiment of the invention, the surface 7 may be water-absorbing, and, as such, may include a compressible and/or porous material such as a sponge or a fibrous non-woven material. In another notable embodiment, the device 1 is a massaging device, useful to provide an active component to the skin. In this embodiment of the invention, the surface 7 may be water-absorbing, and, as such, may include a compressible and/or porous material such as a sponge or a fibrous non-woven material.

Figure 2:
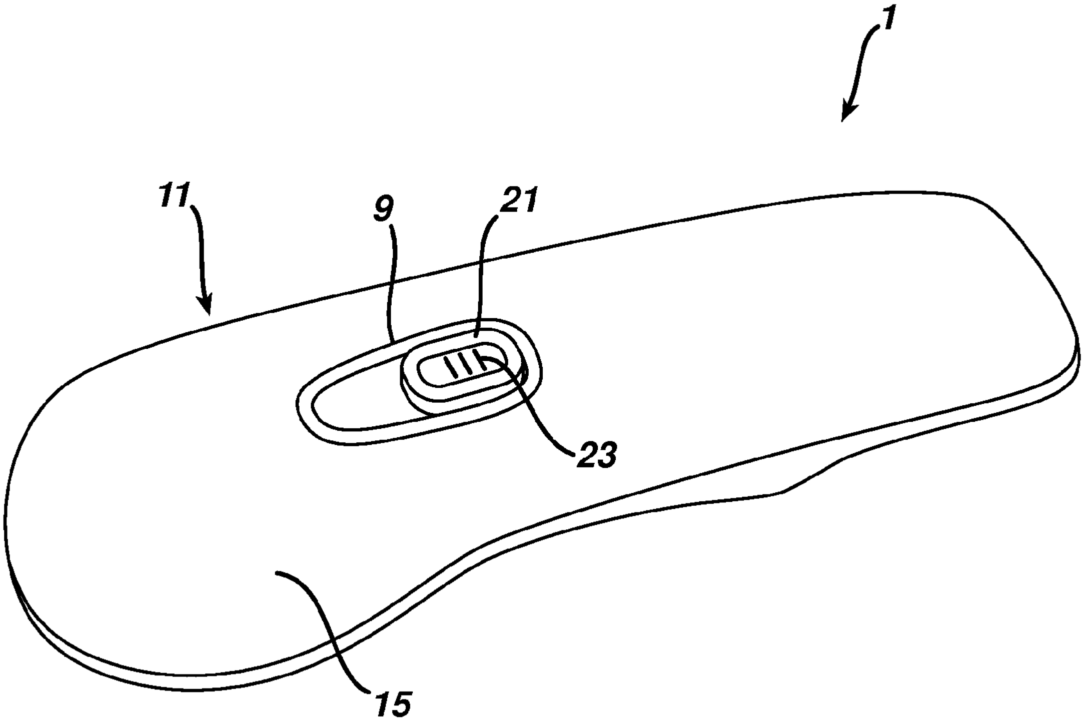
FIG. 2 is another top perspective view of the device of FIG. 1 showing additional features thereof.

As illustrated in FIGS. 1 and 2, the device includes a housing 11, e.g., formed of a hard, lightweight plastic material. As seen in FIG. 1, the housing 11 may be formed of two portions 13 and 15 attached along a seam 17. Additionally, the housing 11 may have a battery compartment accessed through a door panel (not shown, e.g. on the side of the elongate body or handle opposite the switch 9). The water resistance of the seam 17 and the door panel may be increased through the use of a gasket or seal, such as an elastomeric "o-ring."

FIG. 2 is a top-perspective view of the device 1 and the switch assembly 9 of FIG. 1. As shown in FIG. 2, the housing 11 is designed to house various components within the device 1, to help protect the device 1 from damage due to impact, as well as to exclude water and environmental challenges that may adversely affect the device 1. As shown in the Figure, switch assembly 9 is formed on one portion 13 of the housing 11 and includes a switch cover 21 that may be equipped with friction elements 23 to aid an operator's ability to actuate the switch 21 into a particular position. The switch cover 21 may be slideable into one of a plurality of discrete switch positions, or into any of a continuum of positions.

Figure 3:
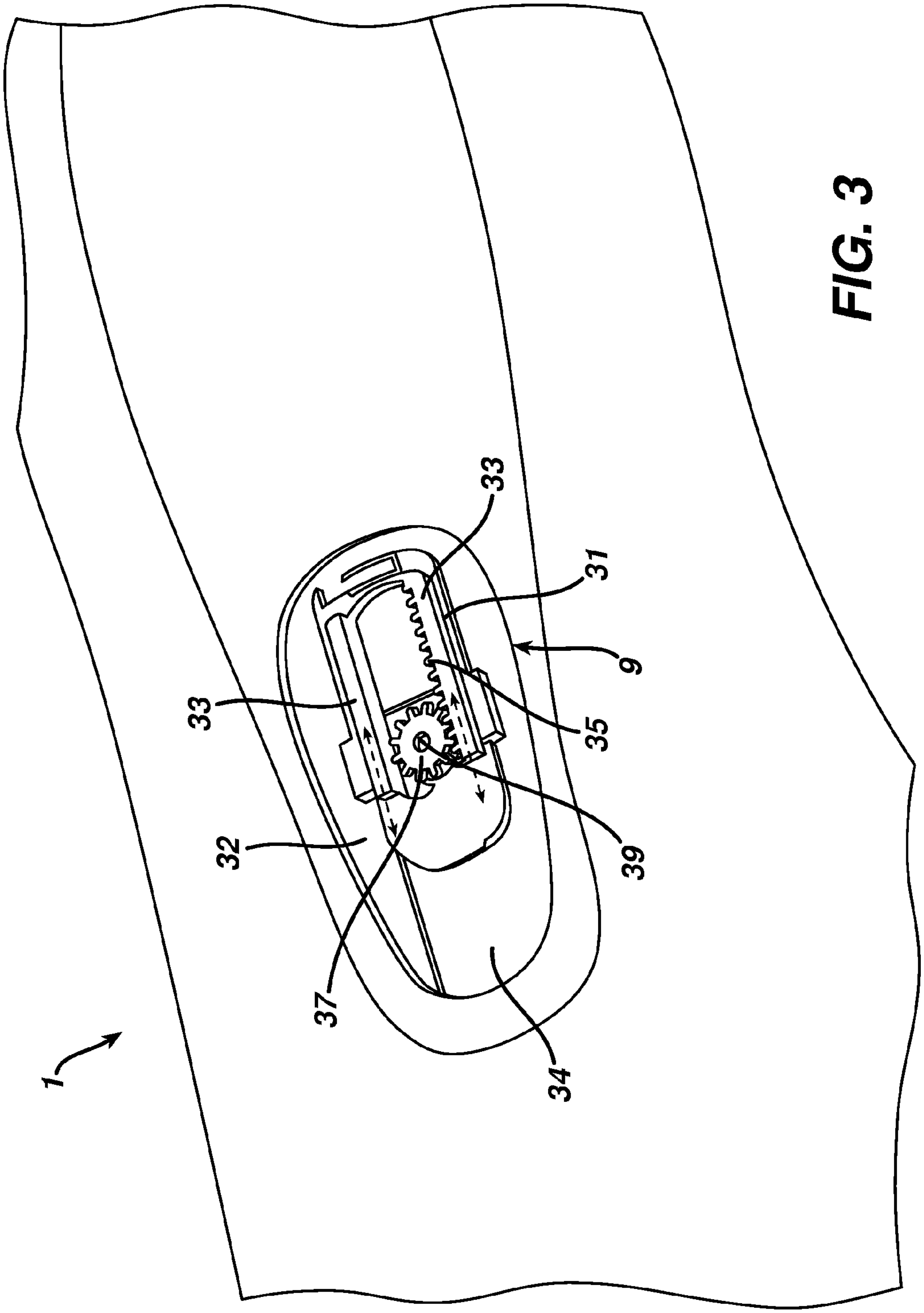
FIG. 3 is another top perspective view of the device of FIG. 1 with a switch cover removed to show features of an embodiment of the switch assembly of the present invention.

FIG. 3 is a close-up, top perspective view of the switch assembly 9 of FIG. 2 with the switch cover 21 removed for clarity. The switch cover 21 (shown in FIG. 2) is in communication with a first translatable element 31. In one embodiment, the switch cover is attached to a top surface 33 of the first translatable element 31. The first translatable element 31 may include, as shown in FIG. 3, a toothed rack or bar. To provide mechanical support to the first translatable element 31, the switch assembly may include a stationary plate 32 that may include a recessed region 34 along which the first translatable element 31 may slide from one position to another.

Upon actuation by an operator, the first translatable element 31 moves from a first position to a second position (in the directions of the arrows shown in FIG. 3). This actuation and the corresponding movement of teeth 35 of the first translatable element 31, effects a corresponding rotational movement of a first pinion gear 37. The first pinion gear 37 engages a rotatable shaft 39. The first pinion gear may be joined to the rotatable shaft 39 such that when the first pinion gear 37 rotates, the rotatable shaft 39 rotates in unison.

Figure 4:
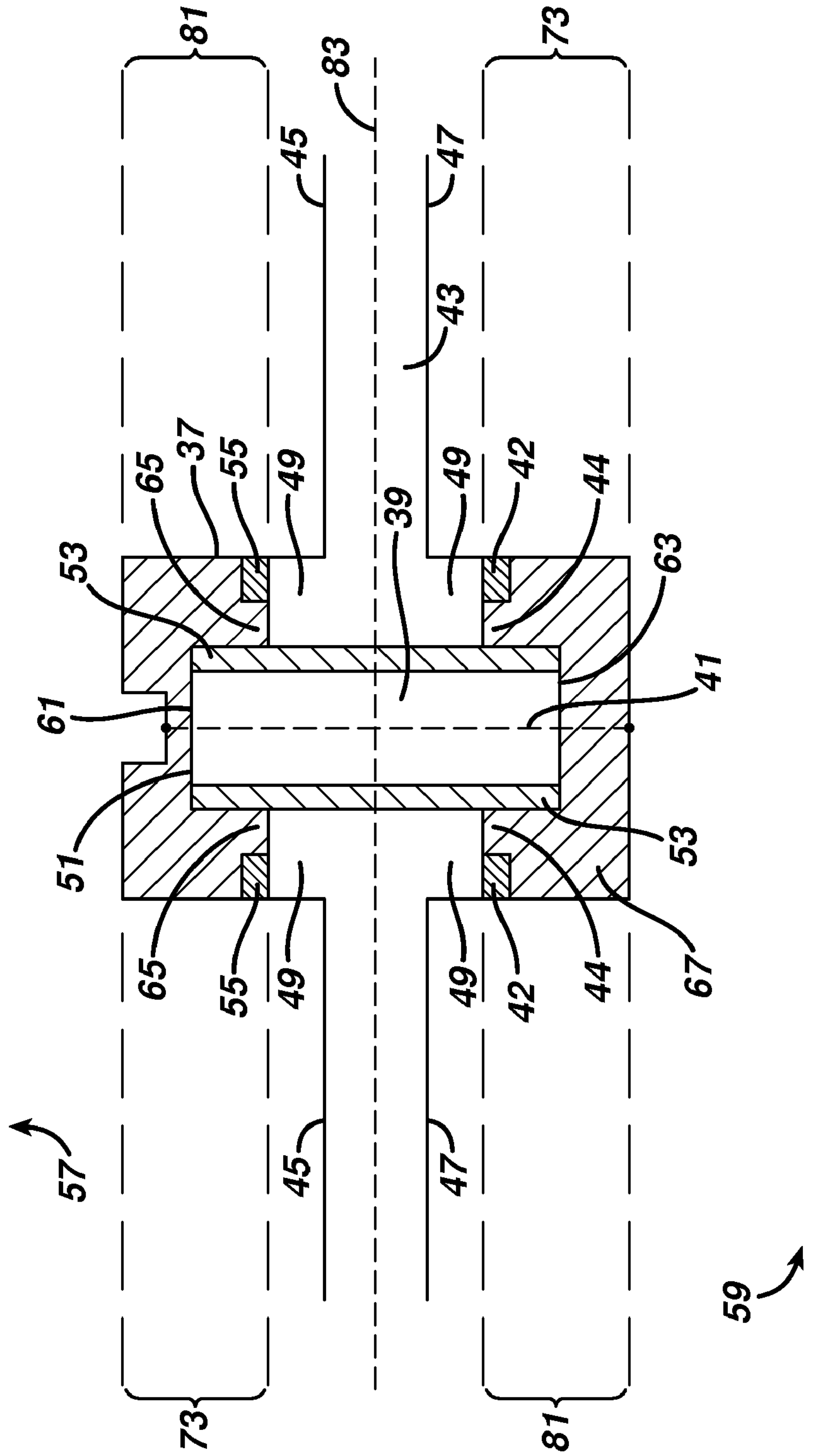
FIG. 4 is a sectional view depicting portions of the switch assembly of the above Figures, the section taken along line 1-1' of FIG. 3.

As shown in the sectional view of FIG. 4, the motion of the first translatable element 31 is preferably substantially planar motion, such as may be substantially within a first plane 73, defined by the movement of the top surface 33 of the first translatable element 31. The rotatable shaft 39 rotates about an axis 41 that is oriented along a direction nonparallel to the first plane 73. In one embodiment of the invention, the axis 41 is substantially normal to the first plane 73.

In one embodiment of the invention, the switch assembly includes a mount 43 that may be substantially planar. Mount 43 includes an upper surface 45 and a lower surface 47 and flanges 49 for spacing the first translatable element 31 apart from the upper surface 45, and to allow for ease of translation of the first translatable element 31. The mount may also provide mechanical support to the stationary plate 32 described above with reference to FIG. 3.

The mount 43 includes a through-hole 51 that is defined by a cylindrical wall 53. The through-hole 51 has a vestibule 61 and a terminus 63. The rotatable shaft 39 is positioned within the through-hole 51, e.g., piercing the through hole 51, and filling the space thereof. A first seal 55 is positioned to resist the movement of water from an exterior space 57 (generally defined as space beyond the vestibule 61 of the through-hole 51, through which water from outside the device may be inclined to enter the through-hole 51) to an interior space 59 (generally defined as space beyond the terminus 63 of the through-hole 51, through which water may be inclined to leave the through-hole 51, pass into the interior space 59, and adversely effect components within the device).

The first seal 55 may be of varying configurations known to those skilled in the art. In one exemplary embodiment shown in FIG. 4, the first seal 55 is an o-ring conformed about a flange region 65 of the pinion gear 37. Alternatively the first seal 55 may be conformed about the rotatable shaft 39 or otherwise shaped and/or configured to seal the through-hole 51. The first seal 55 may be formed of suitable materials, such as those that are flexible or elastomeric (e.g., natural or synthetic rubber and the like) in order to provide a watertight seal.

As shown in FIG. 4, a second pinion gear 67 is engaged to the rotatable shaft 39 such that the rotation of the rotatable shaft 39 about the axis 41 effects a corresponding rotation of the second pinion gear 67 that may be joined to the rotatable shaft 39 as described above with reference to the first pinion gear 37. A second seal 56 may be positioned about a flanged region 44 of the second pinion gear 67 or about the shaft 39, similarly to that described for the first seal. Alternatively either the first seal 55 or the second seal 56 are omitted, i.e., both seals are not required.

Figure 5:
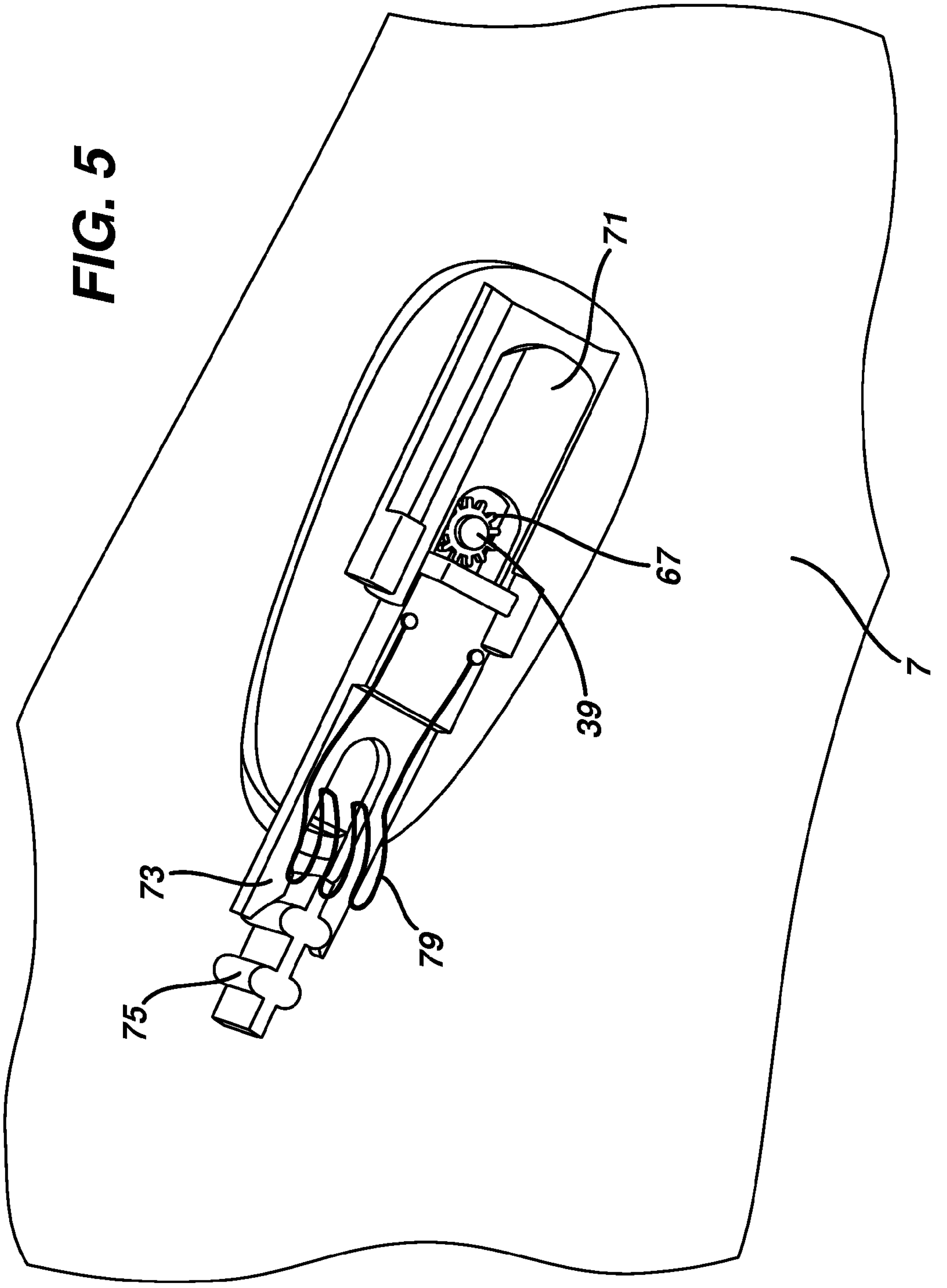
FIG. 5 is a bottom perspective view of an interior portion of the device of FIG. 1, showing additional features of the switch assembly of FIG. 3.

FIG. 5 depicts a bottom perspective view of an interior portion of the device 1, showing the second pinion gear 67 joined to the shaft 39. The second pinion gear is engaged with a second translatable element 71. Similarly to the first translatable element 31, the second translatable element 71 may include a toothed bar or other suitable means to engage the second pinion gear 67. The second translatable element 71 may include a locking element 73 that mates with a molded detent 75 formed on an interior surface 77 of the housing 11. The locking element 73 and detent 75 cooperate to lock the position of the second translatable element 71 into a plurality of discrete positions. Furthermore, the second translatable element 71 may include an electrically conductive element 79 that is joined to and forms a part of the second translatable element 71. Upon movement of the second translatable element 71 from one position to another, a change in electrical potential of the electrically conductive element is effected so as to, for example, adjust the speed of a motor within the device 1. Applicants have noted that in order to reduce the space requirements of the switch assembly, the electrically conductive element 79 may move in a plane that is substantially parallel to the second translatable element 71.

Referring again to FIG. 4, movement of the first translatable element 31 may be contained substantially within the first plane 73, for example defined between a top and bottom surface of the first pinion gear 37. Similarly, movement of the second translatable element 71 may be contained substantially within a second plane 81 (different from the first plane 73), for example defined between a top and bottom surface of the second pinion gear 67. A third plane 83, defined by the center of the substantially planar mount, generally separates first plane 73 and second plane 81. The rotatable shaft 39 desirably pierces (i.e., passes through) the third plane 83.

Embodiments of the present invention are advantageous in the switch assembly is easy to manufacture, inexpensive, and provides waterproofing without occupying a large amount of valuable interior space within the device 1. Furthermore, in certain embodiments of the present invention, inventive devices permit a user to contact her skin with a pleasant surface that can be run under water, provide mechanical action to the skin, and still maintain water-resistance.

From the foregoing description, one skilled in the art can ascertain the essential characteristics of this invention, and, without departing from the spirit and scope thereof can make various changes and modifications. Embodiments set forth by way of illustration are not intended as limitations of the variations possible in practicing the present invention.

What is claimed is:

1. An electric-powered skin treatment device comprising:

a) a housing formed of at least two rigid elements joined along a gasketed seam and comprising an elongate handle portion b) a water-resistant switch assembly and c) a head region coupled to the housing and having disposed thereon at least one surface useful for skin treatment, the surface arranged and configured to deliver relative motion to the skin, wherein the water-resistant switch assembly comprises (1) a first translatable element disposed on a substantially planar mount formed in one of the at least two rigid elements of the housing, and the substantially planar mount has an aperture, a rotatable shaft extending through the aperture having mounted thereon an exterior gear that is engageable with the first translatable element, and a seal lining the aperture to restrict water movement along the shaft and into an interior of the housing and (2) a second translatable element disposed in the interior of the housing and engageable with an interior gear mounted on the rotatable shaft, the first translatable element capable of linear movement along a first axis and the second translatable element capable of linear movement along a second axis, substantially parallel the first axis, and wherein the linear movement of the first translatable element is transferred to rotational movement of the rotatable shaft via the exterior gear and the rotational movement of the rotatable shaft is transferred to the linear movement of the second translatable element via the interior gear.

2. A water-resistant device, comprising:

a) a skin-contactable surface comprising a water-absorbing material; and b) a body having a switch assembly, comprising:

i) a rotatable shaft having mounted thereon a first pinion gear and a second pinion gear;

ii) a first translatable element comprising a first rack engageable with the first pinion gear disposed on a substantially planar mount having a through-hole, wherein said rotatable shaft pierces said through-hole; and iii) a seal surrounding said through-hole for rendering said through hole water-resistant; and iv) a second translatable element comprising a second rack engageable with the second pinion gear disposed in an interior of the body, the first translatable element capable of linear movement along a first axis and the second translatable element capable of linear movement along a second axis, substantially parallel the first axis;

wherein the linear movement of the first translatable element is transferred to rotational movement of the rotatable shaft via the first pinion gear and the rotational movement of the rotatable shaft is transferred to the linear movement of the second translatable element via the second pinion gear.

3. A water-resistant device of claim 2, wherein said skin-contactable surface is compressible.

4. A water-resistant device of claim 2, wherein said skin-contactable surface comprises a sponge or a fibrous material.

* * * * *

UNITED STATES PATENT AND TRADEMARK OFFICE

CERTIFICATE OF CORRECTION

| | |
|---|---|
| PATENT NO. | : 7,918,862 B2 |
| APPLICATION NO. | : 11/287560 |
| DATED | : April 5, 2011 |
| INVENTOR(S) | : Raymond J. Hull, Jr. et al. |

It is certified that error appears in the above-identified patent and that said Letters Patent is hereby corrected as shown below:

On the Title Page, Item (75) Inventors should read:

Raymond J. Hull, Jr., Hampton, NJ (US);
Lau Shu Wong, New Territories (HK)

Signed and Sealed this
Twenty-seventh Day of September, 2011

David J. Kappos

David J. Kappos
*Director of the United States Patent and Trademark Office*